(12) United States Patent
Nakamori et al.

(10) Patent No.: US 10,500,223 B2
(45) Date of Patent: Dec. 10, 2019

(54) THERAPEUTIC AGENT FOR MYOTONIC DYSTROPHY

(71) Applicant: Osaka University, Osaka (JP)

(72) Inventors: Masayuki Nakamori, Osaka (JP); Hideki Mochizuki, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/743,622

(22) PCT Filed: Jul. 7, 2016

(86) PCT No.: PCT/JP2016/070067
§ 371 (c)(1),
(2) Date: Jan. 10, 2018

(87) PCT Pub. No.: WO2017/010382
PCT Pub. Date: Jan. 19, 2017

(65) Prior Publication Data
US 2018/0200277 A1    Jul. 19, 2018

(30) Foreign Application Priority Data
Jul. 14, 2015   (JP) ................. 2015-140599

(51) Int. Cl.
| A61K 31/7048 | (2006.01) |
| A61K 31/7052 | (2006.01) |
| A61P 21/00   | (2006.01) |

(52) U.S. Cl.
CPC ...... *A61K 31/7048* (2013.01); *A61K 31/7052* (2013.01); *A61P 21/00* (2018.01)

(58) Field of Classification Search
None
See application file for complete search history.

(56) References Cited

U.S. PATENT DOCUMENTS

| 5,760,010 | A * | 6/1998 | Klein ................. | A61K 31/7048 514/29 |
| 7,189,703 | B2 * | 3/2007 | Balin .................... | A61K 31/00 514/152 |
| 2005/0137181 | A1 * | 6/2005 | Bonner ................ | A61K 31/198 514/192 |
| 2010/0190689 | A1 * | 7/2010 | Thornton ............. | C12N 15/113 514/6.9 |
| 2013/0112197 | A1 * | 5/2013 | Kruner ................. | A61M 11/005 128/203.12 |
| 2013/0296314 | A1  | 11/2013 | Borody et al. | |
| 2014/0243378 | A1 * | 8/2014 | Draper ................. | A61K 31/11 514/354 |
| 2015/0328247 | A1  | 11/2015 | Rosin-Arbesfeld et al. | |

FOREIGN PATENT DOCUMENTS

| JP | 2014-502598 A | 2/2014 |
| WO | WO 2011/007866 A1 | 1/2011 |
| WO | WO 2014/102778 A2 | 7/2014 |

OTHER PUBLICATIONS

Cell proliferation inhibitory effects of spiramycin. Matsuda, Goto, Saito, Kobayashi and Kakagawa, Japanese Journal of Antibiotics (2003), vol. 56(Suppl. A), 121-123. ISSN: 0368-2781 (Year: 2003).*

International Preliminary Report on Patentability for PCT/JP2016/070067.

Udd, B. et al., "The myotonic dystrophies: molecular, clinical, and therapeutic challenges" Lancet Neurology, 2012, pp. 891-905, vol. 11, No. 10.

Supplementary European Search Report for EP 16824362 dated Feb. 1, 2019.

Aslanidis, Charalampos et al., "Cloning of the essential myotonic dystrophy region and mapping of the putative defect" Nature, Feb. 1992, pp. 548-551, vol. 355.

Brook, J. David et al., "Molecular Basis of Myotonic Dystrophy: Expansion of a Trinucleotide (CTG) Repeat at the 3' End of a Transcript Encoding a Protein Kinase Family Member" Cell, Feb. 1992, pp. 799-808, vol. 68.

Buxton, Jessica et al., "Detection of an unstable fragment of DNA specific to individuals with myotonic dystrophy" Nature, Feb. 1992, pp. 547-548, vol. 355.

Coonrod, Leslie A. et al., "Reducing Levels of Toxic RNA with Small Molecules" ACS Chemical Biology, 2013, pp. 2528-2537, vol. 8.

Harper, Peter S. et al., "Myotonic Dystrophy" Engel AG, Franzini-Armstrong C (eds) Myology, 3rd edn, 2004, pp. 1039-1076.

Liquori, Christina L. et al., "Myotonic Dystrophy Type 2 Caused by a CCTG Expansion in Intron 1 of ZNF9" Science, Aug. 2001, pp. 864-867, vol. 293.

Nakamori, Masayuki et al., "Stabilization of Expanded (CTG)•(CAG) Repeats by Antisense Oligonucleotides" Molecular Therapy, Dec. 2011, pp. 2222-2227, vol. 19, No. 12.

Nakamori, Masayuki et al., "Oral administration of erythromycin decreases RNA toxicity in myotonic dystrophy" Annals of Clinical and Translational Neurology, 2015, pp. 42-54, vol. 3.

Parkesh, Raman et al., "Design of a Bioactive Small Molecule That Targets the Myotonic Dystrophy Type 1 RNA via an RNA Motif-Ligand Database and Chemical Similarity Searching" Journal of the American Chemical Society, 2012, pp. 4731-4742, vol. 134.

Rönnblom, A. et al., "Gastric emptying in myotonic dystrophy" European Journal of Clinical Investigation, 2002, pp. 570-574, vol. 32.

Takahashi, Masanori et al., "Therapeutic development in myotonic dystrophy", Clinical Neurology, 2014, pp. 1077-1079, vol. 54—Abstract.

Warf, M. Bryan et al., "Pentamidine reverses the splicing defects associated with myotonic dystrophy" PNAS, Nov. 2009, pp. 18551-18556, vol. 106, No. 44.

International Search Report for PCT/JP2016/070067 dated Oct. 4, 2016.

* cited by examiner

*Primary Examiner* — Dale R Miller
(74) *Attorney, Agent, or Firm* — Knobbe, Martens, Olson & Bear, LLP (57) ABSTRACT

The present invention provides a therapeutic agent for myotonic dystrophy which inhibits aberrant splicing responsible for myotonic dystrophy, resulting in an increase in a normally spliced product and thus improvement in a symptom of myotonic dystrophy, and is highly safe for use in long-term administration. The therapeutic agent for myotonic dystrophy comprises, as an active ingredient, at least one compound selected from the group consisting of erythromycin, clarithromycin and azithromycin, a pharmaceutically acceptable salt or hydrate thereof, or a prodrug thereof.

2 Claims, 7 Drawing Sheets
Specification includes a Sequence Listing.

Fig. 7 ns5,20009, 0025, 08 on
THERAPEUTIC AGENT FOR MYOTONIC DYSTROPHY

CROSS REFERENCE TO RELATED APPLICATIONS

This application is a U.S. National Phase Application of PCT International Application Number PCT/JP2016/070067, filed on Jul. 7, 2016, designating the United States of America and published in Japanese, which is an International Application of and claims the benefit of priority to Japanese Patent Application No. 2015-140599, filed on Jul. 14, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-IWAT007-002APC.txt, the date of creation of the ASCII text file is Dec. 13, 2017, and the size of the ASCII text file is 1 KB.

TECHNICAL FIELD

The present invention relates to a therapeutic agent for myotonic dystrophy.

BACKGROUND ART

Myotonic dystrophy (hereinafter sometimes referred to as "MyD") is the most common myopathy in adults. MyD is an autosomal dominant multi-organ disorder which affects skeletal and smooth muscles as well as eyeballs, heart, endocrine system and central nervous system, and its symptoms are diverse, including muscular atrophy, muscle weakness, muscle contraction (myotonia), cataract, insulin resistance, hypogonadism, cardiac conduction defect, frontal baldness, intellectual disability, etc. (Non Patent Literature 1). MyD has two types: type I (MyD1) resulting from abnormal expansion of a CTG repeat in the 3'-UTR (3'-untranslated region) of the dystrophia myotonica protein kinase (DMPK) gene (Non Patent Literature 2 to 4); and type II (MyD2) resulting from abnormal expansion of a CCTG repeat in intron 1 of the Zn finger protein 9 (ZNF9) gene (Non Patent Literature 5). In each type, a particular splicing regulator binds to a transcript (mRNA) with an abnormally expanded repeat, and thus a reduced availability of the splicing regulator for normal splicing triggers aberrant splicing.

Patent Literature 1 discloses that 18 compounds including gentian violet inhibited aberrant splicing of at least one of genes associated with myotonic dystrophy. However, there is no disclosure that these compounds can actually improve the symptoms of myotonic dystrophy. There is still no effective and highly safe therapy for myotonic dystrophy, and in the current circumstances, only symptomatic therapies, such as diet therapy, are given to patients depending on the particular symptoms.

CITATION LIST

Patent Literature

Patent Literature 1: WO 2011/007866

Non Patent Literature

Non Patent Literature 1:
Harper, P S and Monckton, D G: Myotonic dystrophy. In Engel A G, Franzini-Armstrong C (eds) Myology, 3rd edn. McGraw-Hill, New York, 2: 1039-1076, 2004

Non Patent Literature 2:
Aslanidis C, et al.: Cloning of the essential myotonic dystrophy region and mapping of the putative defect, Nature, 355: 548-551, 1992

Non Patent Literature 3:
Brook J D, et al.: Molecular basis of myotonic dystrophy: expansion of a trinucleotide (CTG) repeat at the 3' end of a transcript encoding a protein kinase family member, Cell, 68: 799-808, 1992

Non Patent Literature 4:
Buxton J, et al.: Detection of an unstable fragment of DNA specific to individuals with myotonic dystrophy, Nature, 355, 547-548, 1992

Non Patent Literature 5:
Liguori C L, et al.: Myotonic dystrophy type 2 caused by a CCTG expansion in intron 1 of ZNF9, Science, 293, 864-867, 2001

SUMMARY OF INVENTION

Technical Problem

An object of the present invention is to provide a therapeutic agent for MyD which inhibits aberrant splicing responsible for MyD, resulting in an increase in a normally spliced product and thus improvement in a symptom of MyD, and is highly safe for use in long-term administration.

Solution to Problem

In order to achieve the above-mentioned object, the present invention includes the following.
(1) A therapeutic agent for myotonic dystrophy comprising, as an active ingredient, at least one compound selected from the group consisting of erythromycin, clarithromycin and azithromycin, a pharmaceutically acceptable salt or hydrate thereof, or a prodrug thereof.
(2) The therapeutic agent according to the above (1), wherein the therapeutic agent improves muscle contraction.
(3) The therapeutic agent according to the above (1) or (2), wherein the therapeutic agent inhibits aberrant splicing caused by abnormal expansion in a dystrophia myotonica protein kinase (DMPK) gene.
(4) A method for treating myotonic dystrophy, comprising administering, to a mammal, an effective amount of at least one compound selected from the group consisting of erythromycin, clarithromycin and azithromycin, a pharmaceutically acceptable salt or solvate thereof, or a prodrug thereof.
(5) At least one compound selected from the group consisting of erythromycin, clarithromycin and azithromycin, a pharmaceutically acceptable salt or solvate thereof, or a prodrug thereof for use in treatment of myotonic dystrophy.
(6) An inhibitor of aberrant splicing caused by abnormal expansion in a dystrophia myotonica protein kinase (DMPK) gene, the inhibitor comprising, as an active ingredient, at least one compound selected from the group consisting of erythromycin, clarithromycin and azithromycin, a pharmaceutically acceptable salt or solvate thereof, or a prodrug thereof.
(7) The inhibitor according to the above (6), wherein the inhibitor inhibits aberrant splicing of at least one gene selected from the group consisting of ATP2A1, CLCN1, INSR, DMD, MBNL1 and BIN1.

Advantageous Effects of Invention

The present invention provides a therapeutic agent for MyD which can improve a symptom of MyD and is highly safe for use in long-term administration. In addition, the present invention provides an inhibitor of aberrant splicing, which inhibitor remarkably inhibits aberrant splicing caused by abnormal expansion in the dystrophia myotonica protein kinase (DMPK) gene.

DESCRIPTION OF EMBODIMENTS

The present invention provides a therapeutic agent for myotonic dystrophy comprising, as an active ingredient, at least one compound selected from the group consisting of erythromycin, clarithromycin and azithromycin, a pharmaceutically acceptable salt or solvate thereof, or a prodrug thereof.

Erythromycin, which is a 14-membered cyclic macrolide antibiotic with strong antibacterial activity mainly against gram-positive bacteria, was first separated and extracted from the culture medium of *Streptomyces erythreus* by McGuire et al. in 1952. Erythromycin has the structure shown below and its chemical name is (2R,3S,4S,5R,6R, 8R,10R,11R,12S,13R)-5-(3,4,6-trideoxy-3-dimethylamino-β-D-xylo-hexopyranosyloxy)-3-(2,6-dideoxy-3-C-methyl-3-O-methyl-α-L-ribo-hexopyranosyloxy)-6,11,12-trihydroxy-2,4,6,8,10,12-hexamethyl-9-oxopentadecan-13-olide.

[Chem. 1]

Erythromycin has been approved as an ethical drug and commercially sold. Such a commercial erythromycin may be purchased and used in the present invention. Commercial erythromycin preparations contain, as an active ingredient, a prodrug such as a salt form including erythromycin stearate and erythromycin lactobionate, and an ester form including erythromycin ethylsuccinate, and can preferably be used as the erythromycin in the present invention.

Clarithromycin is a semisynthetic macrolide antibiotic (6-O-methylerythromycin A) derived from erythromycin by O-methylation of the hydroxyl group at C-6 position of the lactone ring, and due to the chemical structure, is considered more acid-stable than erythromycin. Clarithromycin has the structure shown below and its chemical name is (2R,3S,4S, 5R,6R,8R,10R,11R,12S,13R)-5-(3,4,6-trideoxy-3-dimethylamino-β-D-xylo-hexopyranosyloxy)-3-(2,6-dideoxy-3-C-methyl-3-O-methyl-α-L-ribo-hexopyranosyloxy)-11,12-dihydroxy-6-methoxy-2,4,6,8,10,12-hexamethyl-9-oxopentadecan-13-olide. Clarithromycin has been approved as an ethical drug and commercially sold. Such a commercial clarithromycin may be purchased and used in the present invention.

[Chem. 2]

Azithromycin is a 14-membered cyclic macrolide antibiotic derived from erythromycin. Azithromycin has the structure shown below and its chemical name is (2R,3S,4S,5R,6R,8R,11R,12R,13S,14R)-5-(3,4,6-trideoxy-3-dimethylamino-β-D-xylo-hexopyranosyloxy)-3-(2,6-dideoxy-3-C-methyl-3-O-methyl-α-L-ribo-hexopyranosyloxy)-10-aza-6,12,13-trihydroxy-2,4,6,8,10,11,13-heptamethylhexadecan-14-olide dihydrate. Azithromycin has been approved as an ethical drug and commercially sold. Such a commercial azithromycin may be purchased and used in the present invention. Azithromycin is preferably used in the form of a hydrate.

[Chem. 3]

Erythromycin, clarithromycin and azithromycin are orally available antibiotics, and due to their long history of clinical use, the safety in long-term administration is guaranteed. Therefore, the present invention can provide a therapeutic agent which is inexpensive, tolerable and highly safe for MyD patients.

In the present invention, the pharmaceutically acceptable salt is not particularly limited as long as it retains the efficacy of the active ingredient without adverse effects on the human body. Examples of the pharmaceutically acceptable salt include salts with acids such as acetic acid, propionic acid, butyric acid, formic acid, trifluoroacetic acid, maleic acid, tartaric acid, citric acid, stearic acid, succinic acid, ethylsuccinic acid, malonic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid (tosyl acid), lauryl sulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer and carboxy vinyl polymer; salts with inorganic bases, such as a lithium salt, a sodium salt, a potassium salt and a calcium salt; salts with organic amines such as morpholine and piperidine; and salts with amino acids.

In the present invention, the prodrug means a compound that is to be converted into erythromycin, clarithromycin or azithromycin by reaction with enzymes, gastric acid, or the like under physiological conditions in the living body. Examples of the prodrug include an ester that is to be hydrolyzed into any of these compounds in the living body.

The therapeutic agent of the present invention can effectively improve a symptom of MyD. MyD is known to have two types. Type I (MyD1) is characterized by abnormal expansion of a CTG repeat in the 3'-UTR of the dystrophia myotonica protein kinase (DMPK) gene, and type II (MyD2) is characterized by abnormal expansion of a CCTG repeat in intron 1 of the Zn finger protein 9 (ZNF9) gene. The disease to be treated with the therapeutic agent of the present invention is not limited to these two types and includes all the conditions diagnosed as MyD. Preferred is type I (MyD1).

The symptom that can be improved by the therapeutic agent of the present invention is not particularly limited, and examples include muscle contraction (myotonia), muscular atrophy, muscle weakness, cardiac lesions (cardiac conduction defect, myocardiopathy), central nervous system symptoms (dementia, character change, somnolence), eye symptoms (cataract, retinal degeneration) and endocrinopathy (impaired glucose tolerance, hyperlipidemia). Preferred are muscle contraction (myotonia), muscular atrophy and muscle weakness, and more preferred is muscle contraction (myotonia).

The therapeutic agent of the present invention can inhibit aberrant splicing caused by abnormal expansion in the dystrophia myotonica protein kinase (DMPK) gene. The aberrant splicing means that splicing, a process of removing introns from a precursor mRNA to join exons together, does not normally proceed, resulting in the generation of aberrantly spliced products. To inhibit aberrant splicing means to partially or completely inhibit the generation of aberrantly spliced products, resulting in increased generation of the normally spliced product (normal mRNA).

The genes of which the aberrant splicing occurs due to abnormal expansion in the DMPK gene include the genes shown in the following Table 1 (Nakamori M, et al.: ANN NEUROL 2013; 74: 862-872).

TABLE 1

| Gene symbol | Exon/intron to be affected |
| --- | --- |
| ABLIM2 | exon 12 |
| ALPK3 | exon 2 |
| ANK2 | exon 21 |
| ARFGAP2 | exon 6$^a$ |
| ATP2A1 | exon 22 |
| ATP2A2 | intron 19 |
| BIN1 | exon 11 |
| CACNA1S | exon 29 |
| CAMK2B | exon 13$^a$ |
| CAPN3 | exon 16 |
| CAPZB | exon 8 |
| CLCN1 | exon 7a |
| COPZ2 | exon 9b |
| DMD | exons 71, 78 |
| DTNA(DB1) | exons 11a, 12 |
| DTNA(DB2) | exons 11a, 12 |
| FHOD1 | exon 11a |
| GFPT1 | exon 9 |
| IMPDH2 | exon 9b |
| INSR | exon 11$^a$ |
| KIF13A | exon 32 |
| LDB3 | exons 5, 11 |
| NBNL1 | exon 7 |
| MLF1 | exon 3 |
| NFIX | exon 7 |
| NRAP | exon 12 |
| OPA1 | exon 4b |
| PDLIM3 | exon 5 |
| PHKA1 | exons 19, 28 |
| RYR1 | exon 70$^a$ |
| SOS1 | exon 25 |
| TBC1D15 | exon 10 |

TABLE 1-continued

| Gene symbol | Exon/intron to be affected |
|---|---|
| TTN | exon Mex5$^a$ |
| TXNL4A | exon 4 |
| UBE2D3 | exon 10 |
| USP25 | exons 19a, 19b |
| VEGFA | exons 6a, 6b |
| VPS39 | exon 3 |

The therapeutic agent of the present invention can be prepared in a dosage form by blending the above-mentioned active ingredient with a pharmaceutically acceptable carrier and an additive as appropriate. Specific examples of the dosage form include oral preparations such as tablets, coated tablets, pills, powders, granules, capsules, solutions, suspensions and emulsions; and parenteral preparations such as injections, infusions, suppositories, ointments and patches. The blending ratio of the carrier or the additive can be determined as appropriate based on the range of the blending ratio conventionally adopted in the pharmaceutical field. The carrier or the additive that can be added is not particularly limited, and examples include various carriers such as water, physiological saline, other aqueous solvents, and aqueous or oily bases; and various additives such as fillers, binders, pH adjusters, disintegrants, absorption enhancers, lubricants, colorants, corrigents and flavors.

Examples of the filler include lactose, sucrose, D-mannitol, starch, crystalline cellulose and light silicic acid anhydride. Examples of the binder include high-molecular-weight compounds such as crystalline cellulose, sucrose, D-mannitol, dextrin, hydroxypropyl cellulose, hydroxypropyl methylcellulose and polyvinyl pyrrolidone. Examples of the lubricant include magnesium stearate, calcium stearate, talc and colloidal silica. Examples of the disintegrant include starch, carboxymethyl cellulose, calcium carboxymethyl cellulose, croscarmellose sodium and sodium carboxymethyl starch. Examples of the wetting agent include glycerin, butylene glycol, propylene glycol, sorbitol and triacetin. These are all non-limiting examples. If needed, the therapeutic agent may be covered with a coating material (sucrose, gelatin, hydroxypropyl cellulose, hydroxypropyl methylcellulose phthalate, etc.) or with two or more coating layers.

When the therapeutic agent of the present invention is an injection, the injection can be prepared by dissolving or dispersing the active ingredient in an aqueous base such as physiological saline or an oily base acceptable for injection, and used as an injection for intravenous, intramuscular or subcutaneous administration. The injection further contains an additive such as a buffering agent, a pH adjuster, a tonicity agent, a solubilizing agent, a suspending agent and a stabilizing agent as needed.

Examples of the aqueous base used for the preparation of the injection include liquid for infusion, such as physiological saline, water for injection and Ringer's solution. Examples of the oily base include propylene glycol, polyethylene glycol, sesame oil, soybean oil, corn oil, peanut oil, cottonseed oil, olive oil and propylene glycol fatty acid ester. Examples of the buffering agent include buffer solutions such as phosphate buffer, acetate buffer, carbonate buffer, citrate buffer, borate buffer, glutamate buffer, ε-aminocaproate buffer and Tris buffer. Examples of the pH adjuster include inorganic acids such as hydrochloric acid, phosphoric acid, sulfuric acid and carbonic acid; organic acids such as acetic acid, tartaric acid, lactic acid, citric acid, tartaric acid and succinic acid; inorganic bases such as sodium hydroxide; and organic bases such as sodium citrate and sodium tartrate. Examples of the tonicity agent include inorganic salts such as sodium chloride; sugar alcohols such as D-mannitol, sorbitol and xylitol; saccharides such as fructose, glucose, galactose, ribose, xylose, mannose, maltotriose and maltoteraose; and amino acids such as glycine and arginine. Examples of the solubilizing agent include polyethylene glycol, propylene glycol, D-mannitol, benzyl benzoate, ethanol, tris aminomethane, cholesterol, triethanolamine, sodium carbonate, sodium citrate, lecithin and nonionic surfactants such as polysorbate 80. Examples of the suspending agent include surfactants such as stearyl triethanolamine, sodium lauryl sulfate, lauryl aminopropionic acid, lecithin and glyceryl monostearate; and others such as polyvinyl alcohol, polyvinyl pyrrolidone, sodium carboxymethyl cellulose, methyl cellulose and hydroxymethyl cellulose. Examples of the stabilizing agent include albumin, globulin, gelatin, sorbitol, ethylene glycol, propylene glycol and ascorbic acid.

Since the active ingredient of the therapeutic agent of the present invention has a long history of clinical use, the therapeutic agent can be safely administered to humans and other mammals (e.g., rats, mice, rabbits, sheep, pigs, cattle, cats, dogs, monkeys, etc.).

The daily dose of the pharmaceutical composition of the present invention is not particularly limited as long as the dose is effective for the treatment of MyD while causing few side effects. The daily dose of the pharmaceutical composition of the present invention is preferably determined according to the daily dose of commercial erythromycin, clarithromycin or azithromycin.

The present invention also provides an inhibitor of aberrant splicing caused by abnormal expansion in the dystrophia myotonica protein kinase (DMPK) gene. As with the therapeutic agent of the present invention, the inhibitor of the present invention can comprise, as an active ingredient, at least one compound selected from the group consisting of erythromycin, clarithromycin and azithromycin, a pharmaceutically acceptable salt or solvate thereof, or a prodrug thereof.

Examples of the genes of which the aberrant splicing can be inhibited by the inhibitor of the present invention include the genes shown in Table 1 above. In particular, inhibiting aberrant splicing of the gene ATP2A1, CLCN1, INSR, DMD, MBNL1, BIN1, or the like is preferred, and inhibiting aberrant splicing of ATP2A1 or CLCN1 is more preferred.

The present invention further includes the following.

A method for treating myotonic dystrophy, comprising administering, to a mammal, an effective amount of at least one compound selected from the group consisting of erythromycin, clarithromycin and azithromycin, a pharmaceutically acceptable salt or solvate thereof, or a prodrug thereof.

At least one compound selected from the group consisting of erythromycin, clarithromycin and azithromycin, a pharmaceutically acceptable salt or solvate thereof, or a prodrug thereof for use in treatment of myotonic dystrophy.

Use of at least one compound selected from the group consisting of erythromycin, clarithromycin and azithromycin, a pharmaceutically acceptable salt or solvate thereof, or a prodrug thereof for production of a therapeutic agent for myotonic dystrophy.

A method for inhibiting aberrant splicing caused by abnormal expansion in a dystrophia myotonica protein kinase (DMPK) gene, the method comprising administering, to a mammal, an effective amount of at least one compound selected from the group consisting of erythromycin, clarithromycin and azithromycin, a pharmaceutically acceptable salt or solvate thereof, or a prodrug thereof.

At least one compound selected from the group consisting of erythromycin, clarithromycin and azithromycin, a pharmaceutically acceptable salt or solvate thereof, or a prodrug thereof for use in inhibition of aberrant splicing caused by abnormal expansion in a dystrophia myotonica protein kinase (DMPK) gene.

Use of at least one compound selected from the group consisting of erythromycin, clarithromycin and azithromycin, a pharmaceutically acceptable salt or solvate thereof, or a prodrug thereof for production of an inhibitor of aberrant splicing caused by abnormal expansion in a dystrophia myotonica protein kinase (DMPK) gene.

EXAMPLES

Hereinafter, the present invention will be illustrated in detail by examples, but the present invention is not limited thereto.

Example 1: Effect of Erythromycin on RNA Foci Formation in MyD Model Cells

Figure 1:
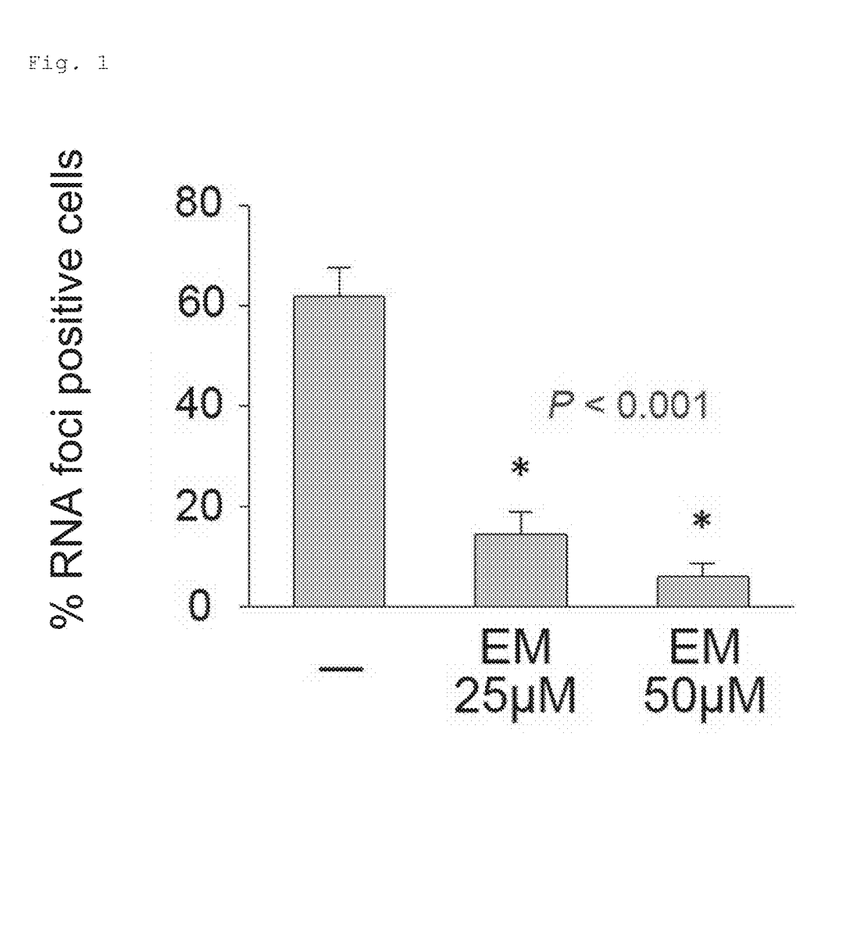
FIG. 1 shows the results of the examination of the effect of erythromycin on RNA foci formation in MyD model cells.

MyD model cells were treated with erythromycin, and the number of RNA foci was measured by the FISH (fluorescence in situ hybridization) method.
Experimental Materials and Methods
(1) MyD Model Cells The MyD cell model used was cells established by transfection of a DMPK gene containing 800 CTG repeats into C2C12 cells (C2C12-DMPK800R, Nucleic Acids Research, 2014, 42 (10), 6591-6602). The establishment of the C2C12-DMPK800 cells was performed in the following procedure. Both a plasmid (pLC16) with a DMPK gene sequence containing 800 CTG repeats in the 3'-untranslated region and a plasmid expressing PhiC31 integrase were transfected into the C2C12 mouse myoblast cell line using Nucleofector (trade name, Lonza), and stably expressing cells were selected using a selection medium with puromycin. Next, a plasmid expressing Cre recombinase was transfected into the stably expressing cells, and a clone in which the transcription of 800 CUG had been activated was selected using a selection medium with hygromycin.
(2) Erythromycin The erythromycin used was "Erythrocin (registered trademark) for intravenous injection 500 mg (erythromycin lactobionate for injection)" (Abbott). This product was dissolved in 10 mL of ultrapure water and then diluted at 15 mg/mL in physiological saline before use.
(3) Determination of Number of Formed RNA Foci The MyD model cells were cultured in DMEM medium supplemented with 10% FBS and penicillin/streptomycin under the conditions of 37° C. and 5% $CO_2$. To the medium, erythromycin was added at 0, 25 or 50 µM, and after 72 hours, the cells were fixed with 3% paraformaldehyde at room temperature for 15 minutes. After the fixation, the cells were washed twice with PBS and then subjected to permeabilization with PBS containing 0.5% TritonX-100 for 5 minutes. Next, pre-hybridization was performed with 2×SSC buffer containing 30% formamide for 10 minutes. After that, hybridization was performed with 2×SSC buffer containing 30% formamide, 2 µg/mL BSA, 66 µg/mL yeast tRNA, 2 mM vanadyl complex and 1 ng/µL Texas Red CAG probe at 37° C. for 1 hour. Post-hybridization was performed with 2×SSC buffer containing 30% formamide at 42° C. for 30 minutes, followed by washing once with 1×SSC buffer and twice with PBS. After mounting in Vectashield with DAPI (trade name, Vector Laboratories), the number of RNA foci in the nucleus was counted with a fluorescence microscope (Keyence PZ-9000).
Results The results are shown in FIG. 1. As is clear from FIG. 1, the percentage of RNA foci positive cells in the MyD model cells cultured in the medium without erythromycin was more than 60%, but the addition of erythromycin to the medium significantly decreased the percentage of RNA foci positive cells in a dose dependent manner.

Example 2: Effect of Erythromycin on Aberrant Splicing in MyD Model Cells

The MyD model cells were treated with erythromycin, and whether erythromycin would correct aberrant splicing in exon 22 of the Atp2a1 gene was examined.
Experimental Materials and Methods
(1) MyD Model Cells The same MyD model cells as in Example 1 (C2C12-DMPK800R) were used.
(2) Erythromycin The same erythromycin as in Example 1 was used.
(3) Quantification of Spliced Products To the medium of the MyD model cells, erythromycin was added at 0, 25 or 50 µM, and after 72 hours, the total RNA was extracted using RNeasy Mini Plus Kit (trade name, Qiagen). As a control, normal C2C12 cells were cultured in a medium without erythromycin, and the total RNA was similarly extracted. For RT-PCR, SuperScript III First-Strand Synthesis System (Invitrogen) was used to prepare cDNA, and after treatment with RNase H, the segment of interest was amplified using the Atp2a1 exon 22 RT primers shown below. The RT-PCR product was electrophoresed on a 2% agarose gel and then stained using GelRed. The normal PCR product and the aberrant PCR product were separately quantified with an image analyzer (Typhoon 9410, GE). Atp2a1 exon 22 RT primers

```
Fw:
                                       (SEQ ID NO: 1)
GCTCATGGTCCTCAAGATCTCAC

Rv:
                                       (SEQ ID NO: 2)
GGGTCAGTGCCTCAGCTTTG
```

Results

Figure 2:
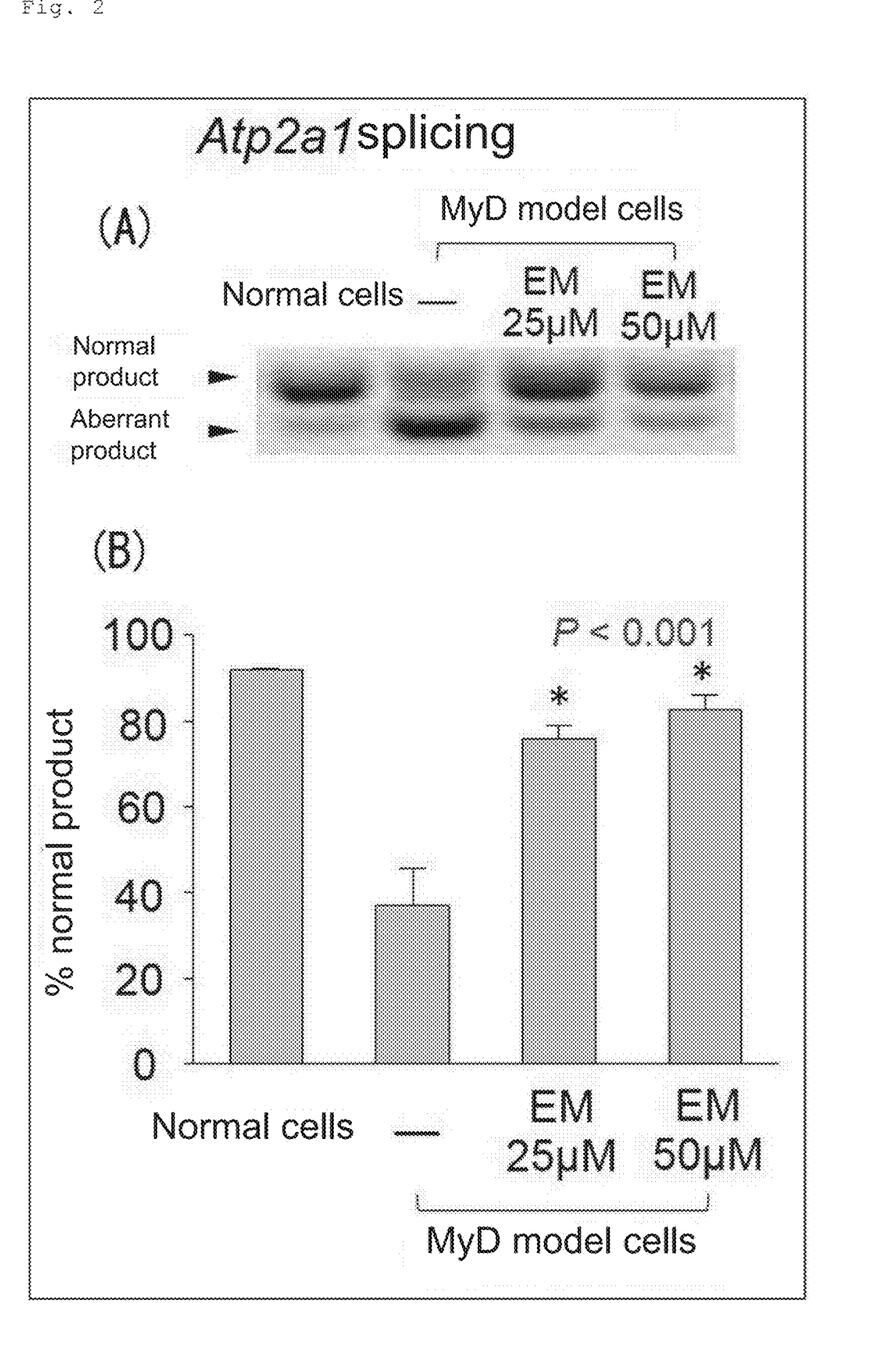
FIG. 2 shows the results of the examination of the effect of erythromycin on aberrant splicing of the Atp2a1 gene in MyD model cells. (A) shows the results of the electrophoresis of a RT-PCR product, and (B) shows the percentage of the normal product in the total RT-PCR product.

The results are shown in FIGS. 2(A) and 2(B). (A) shows the results of the electrophoresis of the RT-PCR product, and (B) is a graph showing the percentage of the normal product in the total RT-PCR product. As shown in FIG. 2(A), in the normal C2C12 cells, the normal product was dominantly detected, but in the MyD model cells cultured in the medium without erythromycin, the percentage of the aberrant product was larger than that of the normal product. The addition of erythromycin to the medium of the MyD model cells significantly increased the percentage of the normal product to a level observed in the normal C2C12 cells, indicating that erythromycin corrects aberrant splicing.

Example 3: Effect of Intraperitoneal Erythromycin in MyD Model Mice

Erythromycin was intraperitoneally administered to MyD model mice, and its effects on muscle contraction in the quadriceps femoris muscle and on aberrant splicing of the skeletal muscle chloride channel (Clcn1) gene in the quadriceps femoris muscle were examined.
Experimental Materials and Methods
(1) Animals Used The MyD model mice used were HSA$^{LR}$ mice, which were kindly provided by Dr. Charles Thornton (University of Rochester) and bred in the laboratory animal facility of Osaka University. The HSA$^{LR}$ mice are transgenic animals prepared by genomic integration of a hACTA gene (human gene constitutively expressed in myocytes) containing 3'-terminal CTG repeats expanded to 220, and manifest the symptoms of MyD upon the expression of mRNA with expanded CUG repeats in the myocytes (Science, 2000, 289 (5485), 1769-73). As a control, wild-type mice (FVB/NJcl mice, purchased from CLEA Japan) were used. Male and female mice aged 8 weeks were used for the experiment.
(2) Erythromycin The erythromycin used was "Erythrocin (registered trademark) for intravenous injection 500 mg (erythromycin lactobionate for injection)" (Abbott). This product was dissolved at 50 mg/mL in physiological saline before use.
(3) Grouping and Administration Schedule The animals were divided into three groups: an erythromycin administration MyD group, a physiological saline administration MyD group and a control (wild-type mice) group (n=3 (1 male, 2 females) per group). The dose of erythromycin was 150 mg/kg, and this dose was repeatedly administered once daily for 8 days. The physiological saline administration MyD group was repeatedly given physiological saline once daily for 8 days. Nothing was administered to the control (wild-type mice) group.
(4) Measurement of Muscle Contraction (Myotonia)

Twenty-four hours after the final administration, needle electromyography was performed in the quadriceps femoris muscle in the mice under anesthesia to record myotonic discharge. Specifically, a needle electrode was inserted into the mouse quadriceps femoris muscle 10 times or more, and the frequency of myotonic discharge was graded on the following four-point scale.
Severity 0:
no myotonic discharge was observed at all.
Severity 1:
myotonic discharge was observed in less than 50% of the needle insertions.
Severity 2:
myotonic discharge was observed in 50% or more and less than 90% of the needle insertions.
Severity 3:
myotonic discharge was observed in 90% or more of the needle insertions.
(5) Quantification of Spliced Products Twenty-four hours after the final administration, the quadriceps femoris muscle was dissected from each mouse. The total RNA was extracted using TRI Reagent (trade name, MRC). For RT-PCR, SuperScript III First-Strand Synthesis System (Invitrogen) was used to prepare cDNA, and after treatment with RNase H, the segment of interest was amplified using the Clcn1 exon 7a RT primers shown below. The RT-PCR product was electrophoresed on a 2% agarose gel and then stained using GelRed. The normal PCR product and the aberrant PCR product were separately quantified with an image analyzer (Typhoon 9410, GE), and the percentage of the normal product in the total RT-PCR product was calculated. Statistical analysis was performed using t-test.

Clcn1 Exon 7a RT Primers

Fw:
(SEQ ID NO: 3)
TGAAGGAATACCTCACACTCAAGG

Rv:
(SEQ ID NO: 4)
CACGGAACACAAAGGCACTG

Results

Figure 3:
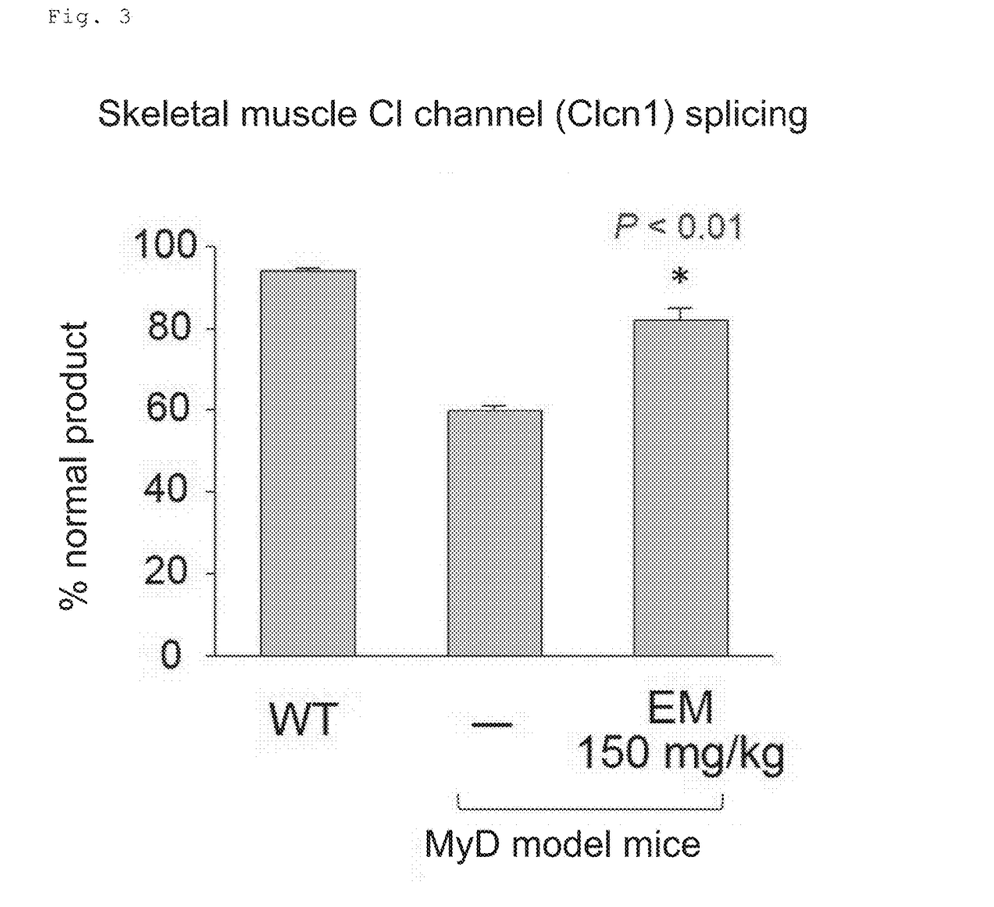
FIG. 3 shows the results of the examination of the effect of erythromycin on aberrant splicing of the skeletal muscle chloride channel (Clcn1) gene in the quadriceps femoris muscle of MyD model mice after 8-day intraperitoneal administration of erythromycin.

The results of the evaluation of aberrant splicing are shown in FIG. 3. In the control group ("WT" in the figure), the normal product accounted for more than 90% of the total RT-PCR product, but in the physiological saline administration MyD group ("-" in the figure), the percentage of the normal product was about 60%, which means an increase in the percentage of the aberrant RT-PCR product. As compared with the physiological saline administration MyD group, the erythromycin administration MyD group showed a significantly higher percentage of the normal RT-PCR product, thereby indicating that the administration of erythromycin corrects the aberrant splicing of the Clcn1 gene.

Figure 4:
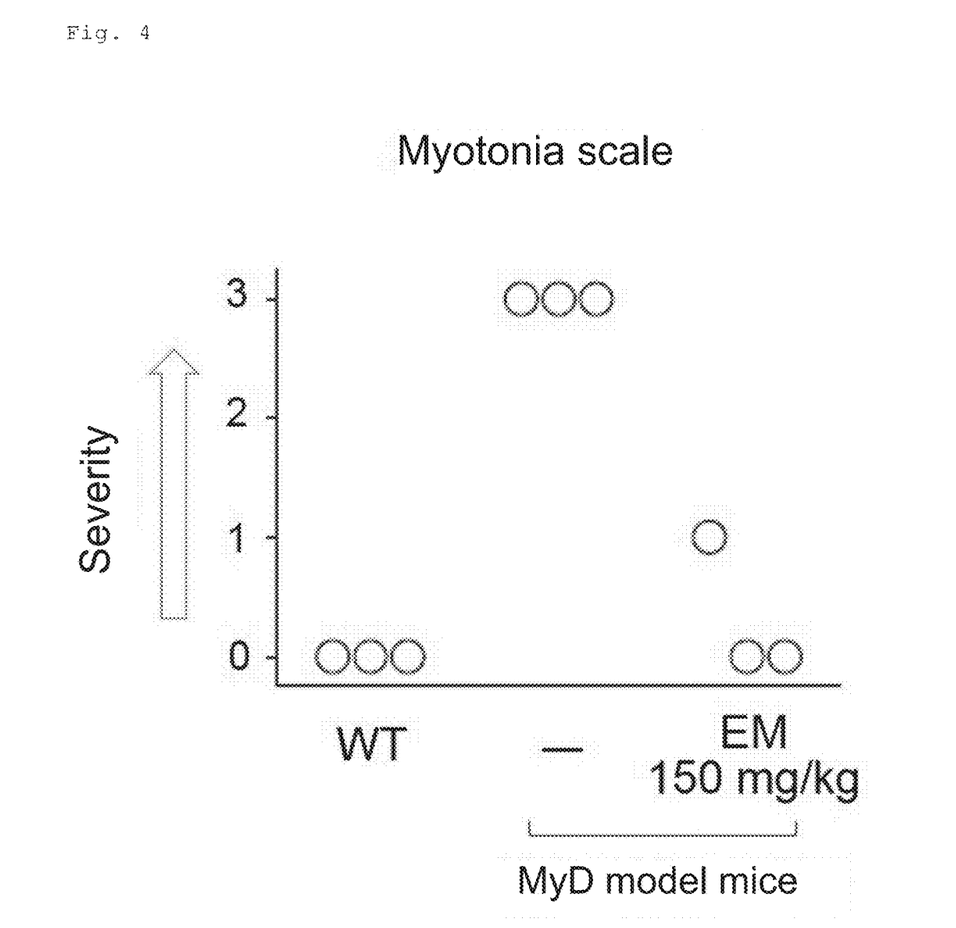
FIG. 4 shows the results of the analysis of muscle contraction (myotonia) in the quadriceps femoris muscle of MyD model mice after 8-day intraperitoneal administration of erythromycin.

The results of the analysis of muscle contraction are shown in FIG. 4. None of the three mice in the control group ("WT" in the figure) showed muscle contraction. In contrast, all the three mice in the physiological saline administration MyD group ("-" in the figure) showed muscle contraction graded as severity 3. In the erythromycin administration MyD group, one mouse showed muscle contraction graded as severity 1 and the other two mice showed no muscle contraction. These results demonstrate that the administration of erythromycin corrects the aberrant splicing caused by abnormal expansion of a CTG repeat and thus improves muscle contraction associated with MyD.

Example 4: Effect of High-Dose Oral Erythromycin in MyD Model Mice

Figure 5:
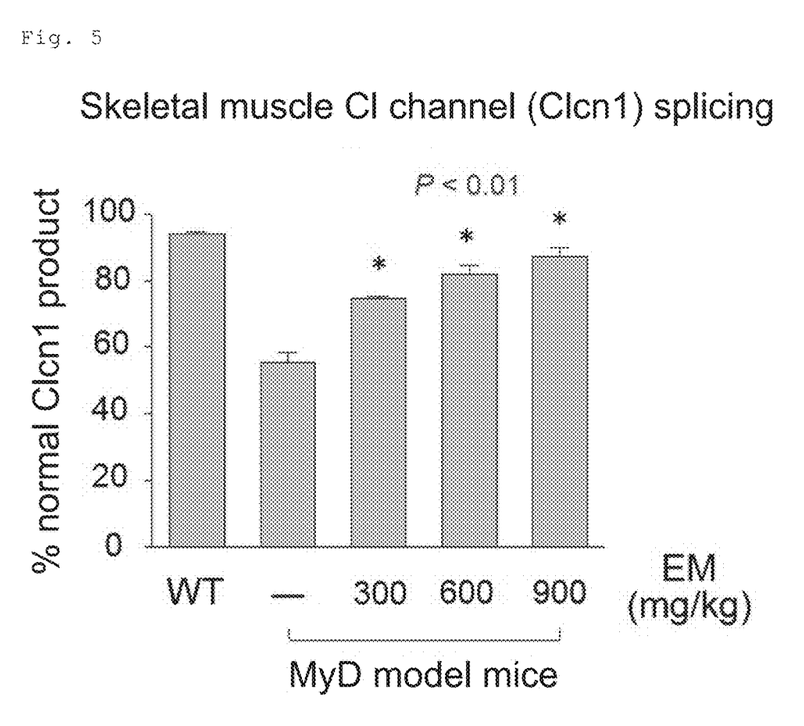
FIG. 5 shows the results of the examination of the effect of erythromycin on aberrant splicing of the skeletal muscle chloride channel (Clcn1) gene in the quadriceps femoris muscle of MyD model mice after 5-day oral administration of high-dose erythromycin.

High-dose erythromycin was orally administered to MyD model mice, and its effect on aberrant splicing of the skeletal muscle chloride channel (Clcn1) gene in the quadriceps femoris muscle was examined.
Experimental Materials and Methods
(1) Animals Used The same MyD model mice (HSA$^{LR}$ mice) and wild-type mice as in Example 3 were used.
(2) Erythromycin The erythromycin used was "Erythrocin (registered trademark) dry syrup W20% (erythromycin ethylsuccinate dry syrup)" (Abbott). This product was dissolved at 100 mg/mL in purified water before use.
(3) Grouping and Administration Schedule The animals were divided into five groups: an erythromycin 300 mg/kg administration MyD group, an erythromycin 600 mg/kg administration MyD group, an erythromycin 900 mg/kg administration MyD group, a physiological saline administration MyD group and a control (wild-type mice) group (n=3 per group). The administration was gavage administration and performed once daily for five consecutive days.
(4) Quantification of Spliced Products On the day of the final administration, the quadriceps femoris muscle was dissected from each mouse. In the same manner as in Example 3, RT-PCR was performed, the normally spliced product and the aberrantly spliced product were separately quantified, and the percentage of the normal product in the total RT-PCR product was calculated. Statistical analysis was performed using t-test.
Results The results are shown in FIG. 5. As is clear from FIG. 5, the high-dose oral erythromycin significantly corrected the aberrant splicing of the Clcn1 gene in a dose dependent manner.

Example 5: Effect of Usual-Dose Oral Erythromycin in MyD Model Mice

Usual-dose erythromycin was orally administered to MyD model mice, and its effects on muscle contraction in the quadriceps femoris muscle and on aberrant splicing of the skeletal muscle chloride channel (Clcn1) gene in the quadriceps femoris muscle were examined.
Experimental Materials and Methods
(1) Animals Used The same MyD model mice ($HSA^{LR}$ mice) and wild-type mice as in Example 3 were used.
(2) Erythromycin As with the case in Example 4, "Erythrocin (registered trademark) dry syrup W20% (erythromycin ethylsuccinate dry syrup)" (Abbott) was dissolved at 100 mg/mL in purified water before use.
(3) Grouping and Administration Schedule The animals were divided into three groups: an erythromycin 50 mg/kg administration MyD group, a physiological saline administration MyD group and a control (wild-type mice) group (n=3 per group). The administration was gavage administration and performed once daily for 21 consecutive days.
(4) Measurement of Muscle Contraction (Myotonia)

On the day of the final administration, needle electromyography was performed in the quadriceps femoris muscle in the mice under anesthesia to record myotonic discharge.

(5) Quantification of Spliced Products

Figure 6:
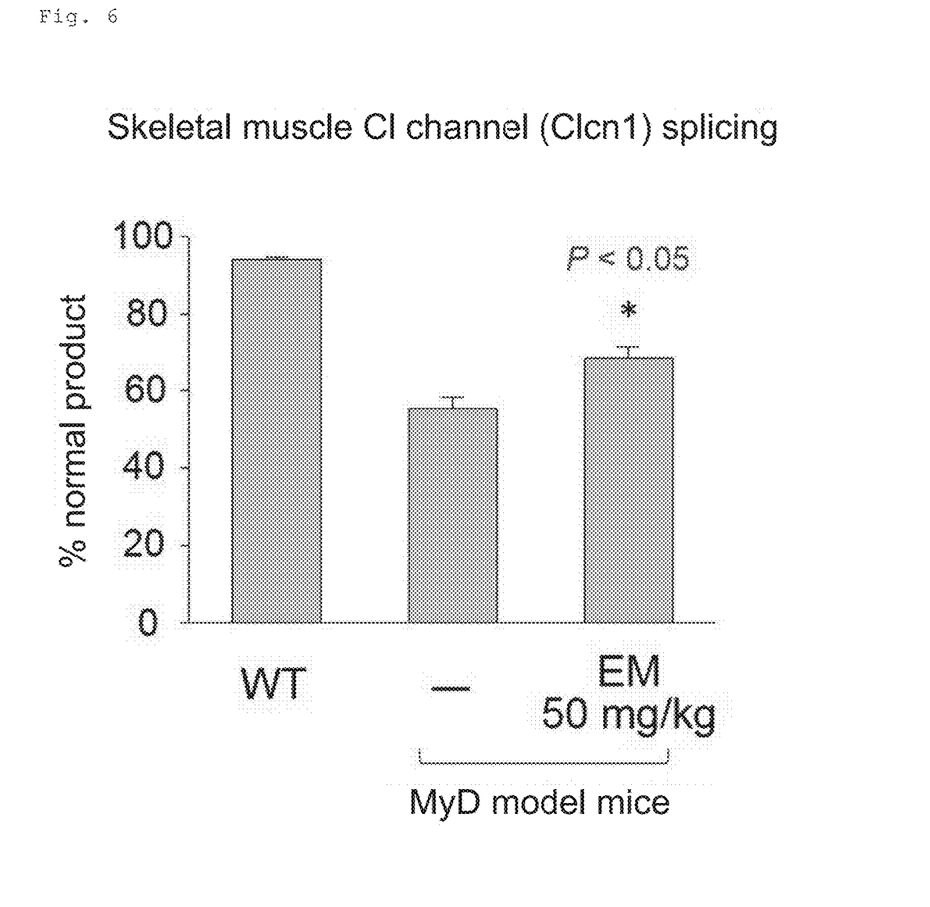
FIG. 6 shows the results of the examination of the effect of erythromycin on aberrant splicing of the skeletal muscle chloride channel (Clcn1) gene in the quadriceps femoris muscle of MyD model mice after 21-day oral administration of usual-dose erythromycin.

On the day of the final administration, the quadriceps femoris muscle was dissected from each mouse. In the same manner as in Example 3, RT-PCR was performed, and the normally spliced product and the aberrantly spliced product were separately quantified. Statistical analysis was performed using t-test.
Results The results of the evaluation of aberrant splicing are shown in FIG. 6. As is clear from FIG. 6, the erythromycin 50 mg/kg administration MyD group showed a significantly higher percentage of the normal RT-PCR product as compared with the physiological saline administration MyD group. That is, the 21-day oral administration of usual-dose erythromycin (50 mg/kg) corrected the aberrant splicing of the Clcn1 gene.

Figure 7:
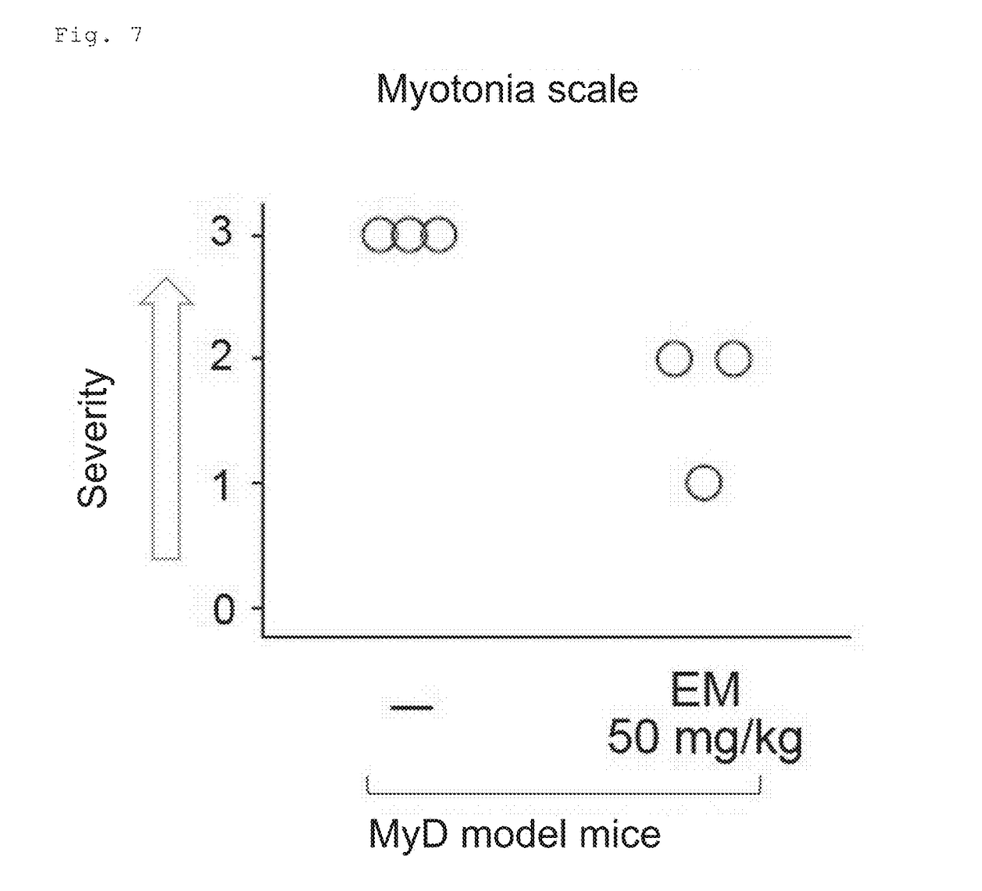
FIG. 7 shows the results of the analysis of muscle contraction (myotonia) in the quadriceps femoris muscle of MyD model mice after 21-day oral administration of usual-dose erythromycin.

The results of the analysis of muscle contraction are shown in FIG. 7. All the three mice in the physiological saline administration MyD group showed muscle contraction graded as severity 3, but in the erythromycin 50 mg/kg administration MyD group, muscle contraction was graded as severity 2 in two mice and as severity 1 in one mouse, and improvement was observed. These results demonstrate that the 21-day oral administration of usual-dose erythromycin (50 mg/kg) corrects the aberrant splicing caused by abnormal expansion of a CTG repeat and thus improves muscle contraction associated with MyD.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for ameliorating at least one symptom of myotonic dystrophy in a mammal that has myotonic dystrophy, comprising:

selecting said mammal, which has myotonic dystrophy and presents at least one symptom of myotonic dystrophy, to receive a compound that ameliorates said at least one symptom of myotonic dystrophy; and administering, to said mammal an effective amount of at least one compound selected from the group consisting of erythromycin, clarithromycin and azithromycin, a pharmaceutically acceptable salt or hydrate thereof, or a prodrug thereof, wherein the at least one symptom of myotonic dystrophy is selected from the group consisting of muscular atrophy, muscle weakness, cardiac conduction defect, myocardiopathy, dementia, somnolence, cataract, retinal degeneration, impaired glucose tolerance and hyperlipidemia.

2. A method for improving muscle contraction in a mammal that has myotonic dystrophy comprising:

selecting a mammal having myotonic dystrophy to receive an agent that improves muscle contraction; and administering to said mammal a composition comprising at least one compound selected from erythromycin, clarithromycin or azithromycin, a pharmaceutically acceptable salt or hydrate thereof, or a prodrug thereof.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
gctcatggtc ctcaagatct cac                23

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
gggtcagtgc ctcagctttg                20

<210> SEQ ID NO 3
<211> LENGTH: 24
<212> TYPE: DNA
<213> ORGANISM: Artificial
<220> FEATURE:
<223> OTHER INFORMATION: Primer

```
<400> SEQUENCE: 3
tgaaggaata cctcacactc aagg                                           24

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
cacggaacac aaaggcactg                                                20
```